(12) United States Patent
Sakaino et al.

(10) Patent No.: US 7,407,578 B2
(45) Date of Patent: Aug. 5, 2008

(54) LIQUID FILTERING INSTRUMENT AND DRY TYPE ANALYSIS DEVICE

(75) Inventors: Yoshiki Sakaino, Asaka (JP); Yukio Sudo, Asaka (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 11/185,822

(22) Filed: Jul. 21, 2005

(65) Prior Publication Data

US 2006/0018798 A1    Jan. 26, 2006

(30) Foreign Application Priority Data

Jul. 23, 2004   (JP)   ............... P.2004-215930

(51) Int. Cl.
*B01D 29/00* (2006.01)

(52) U.S. Cl. ............ 210/416.1; 210/435; 210/450; 210/500.26; 210/503; 210/504; 210/505; 210/506; 210/508; 422/58; 422/101; 422/102; 422/104

(58) Field of Classification Search ......... 210/435, 210/450, 416.1, 500.26, 503, 504, 505, 506, 210/508; 422/101, 58, 102, 104
See application file for complete search history.

(56) References Cited

U.S. PATENT DOCUMENTS

| | | | |
|---|---|---|---|
| 3,682,596 A * | 8/1972 | Stone .................. | 422/101 |
| 3,814,079 A | 6/1974 | Le Roy, Sr. | |
| 4,396,655 A * | 8/1983 | Graham et al. ............. | 428/34.4 |
| 5,364,533 A * | 11/1994 | Ogura et al. ................ | 210/645 |
| 5,725,763 A * | 3/1998 | Bonhomme et al. ......... | 210/188 |
| 5,979,669 A * | 11/1999 | Kitajima et al. ............. | 210/455 |
| 6,217,540 B1 * | 4/2001 | Yazawa et al. ............. | 604/4.01 |
| 6,590,054 B2 * | 7/2003 | Tanaka et al. ............ | 526/328.5 |
| 7,011,755 B2 * | 3/2006 | Zuk, Jr. .................... | 210/416.1 |
| 2006/0016747 A1 * | 1/2006 | Sakaino et al. ............. | 210/450 |

FOREIGN PATENT DOCUMENTS

| | | |
|---|---|---|
| EP | 0 550 950 A2 | 7/1993 |
| JP | 9-196911 A | 7/1997 |
| JP | 10-227788 A | 8/1998 |

OTHER PUBLICATIONS

Iwata Yuzo, "11. Other analytical method (1) dry chemistry," Laboratory Chemical Practice Manual, issued by Igaku-Shoin Ltd. 1996, Issue Number of Kensa To Gijyutsu, vol. 21, No. 5, p. 328-333.

* cited by examiner

*Primary Examiner*—John Kim
(74) *Attorney, Agent, or Firm*—Birch, Stewart, Kolasch & Birch, LLP

(57) ABSTRACT

A liquid filtering instrument 10 according to the present invention achieves filtered liquid by pressure-reduced filtration, and it comprises a filter member 12 in which a liquid filter 15 is accommodated, and a holder member 14 for stocking filtered liquid passed through the liquid filter 15, wherein the filter member 12 and the holder member 14 are formed in capable of being fitted so as to be kept substantially air-tight and water-tight under pressure reduced state.

14 Claims, 7 Drawing Sheets

LIQUID FILTERING INSTRUMENT AND DRY TYPE ANALYSIS DEVICE

BACKGROUND OF THE INVENTION

1. Field of the Invention

The present invention relates to a liquid filtering instrument for filtering liquid, and particularly to a liquid filtering instrument suitably used to prepare blood plasma or blood serum samples from blood of humans or other animals. Furthermore, the present invention relates to a dry type analysis device for filtering body liquid such as blood, urine or the like under reduced pressure and analyzing the body liquid thus filtered.

2. Description of the Related Art

Recently, a compact type filter unit in which a filter is mounted in advance has been frequently used when liquid such as organic solvent or the like is filtered in a chemical experiment.

"Chromatodisc 13N" sold by GL Science Inc. is known as a filter unit which is generally used for chemical experiments. This filter unit uses porous membrane of polytetrafluoroethylene (PTFE) as a filter, and it is designed by unifying plural housing members of polypropylene (PP) into one body through fusion.

When body liquid such as urine, blood or the like is filtered, a compact cartridge type filter unit is used (for example, see Japanese Published Unexamined Patent Application No. H9-196911). The cartridge type filter unit is generally formed as follows. That is, a filter is pinched by plural resin housing members and fused by ultrasonic waves or the like so that the filter and the resin housing members are unified into one body.

Furthermore, there has been developed a filter unit filled with a filter which can separate blood cells to take out blood plasma from whole blood (for example, see Japanese Published Unexamined Patent Application No. H10-227788 (FIG. 1)). Products on the market are known as this filter unit, and for example, "FUJI DRI-CHEM PLASMA FILTER PF" sold from Fujifilm Medical Co., Ltd. is known. This filter unit employs polysulfone (PSF) porous membrane as a filter, and transparent polystyrene (PS) housing members are unified into one body by ultrasonic fusion.

A method of diagnosing disease of humans or other animals while body liquid such as blood, urine or the like is used as a specimen has been carried out for a long time as a simply and easy method of performing diagnosis without damaging human bodies. As one method of analyzing blood, urine or the like has been developed a so-called dry chemistry analysis method which does not use solution, that is, in which a reagent group needed to detect a specific component is contained under a dry state (Yuzo Iwata, "11. Other analytical method (1) dry chemistry," Laboratory Chemical Practice Manual, issued by Igaku-Shoin Ltd. 1993, Issue Number of "Kensa To Gijyutsu," Vol. 21, No. 5, p. 328-333).

SUMMARY OF THE INVENTION

The filter unit as described above is frequently used for chemical experiments, etc., and thus it is desired to reduce the cost thereof. Furthermore, when a filter unit or a dry type analysis device is used to analyze body liquid such as blood, urine or the like, it is frequently subjected to sterilization treatment and then disposal after it is used. Therefore, it is more important to reduce the costs of the filter unit and the dry type analysis device.

An object of the present invention is to provide an inexpensive liquid filtering instrument and dry type analysis device.

The present invention achieves the above object by the following construction.

(1) A liquid filtering instrument for filtering a liquid under pressure-reduced filtration, the liquid filtering instrument comprising:

a filter member receiving a liquid filter; and a holder member that stocks a filtered liquid passing through the liquid filter, wherein the filter member and the holder member are capable of being fitted so as to be substantially air-tight and water-tight when a pressure is reduced.

(2) The liquid filtering instrument as described in (1) above, which further comprises a seal member in a fitting portion between the filter member and the holder member.

(3) The liquid filtering instrument as described in (2) above, wherein the seal member is a porous membrane, and an opening portion of the filter member at an exit side of liquid is covered by the porous membrane.

(4) The liquid filtering instrument as described in any of (1) to (3) above, wherein the liquid filter comprises a fiber having a diameter of 10 µm or less.

(5) The liquid filtering instrument as described in any of (1) to (4) above, wherein the liquid filter comprises a glass fiber.

(6) The liquid filtering instrument as described in (5) above, wherein a surface of the glass fiber is coated with a polymer.

(7) The liquid filtering instrument as described in (5) above, wherein the glass fiber is subjected to an acid treatment, and then a surface of the glass fiber is coated with a polymer.

(8) The liquid filtering instrument as described in (6) or (7) above, wherein the polymer is an acrylate polymer.

(9) The liquid filtering instrument as described in (6) or (7) above, wherein the polymer is a poly(alkoxy acrylate).

(10) The liquid filtering instrument as described in any of (1) to (9) above, wherein the liquid filtering instrument is disposable.

(11) The liquid filtering instrument as described in any of (1) to (10) above, wherein the liquid is a body fluid.

(12) The liquid filtering instrument as described in (11) above, wherein the body fluid is a blood.

(13) The liquid filtering instrument as described in any of (1) to (10) above, wherein the liquid is a liquid for examining an environment-related material.

(14) The liquid filtering instrument as described in any of (1) to (10) above, wherein the liquid is a liquid for examining a food product.

(15) The liquid filtering instrument as described in any of (1) to (10) above, wherein the liquid is a liquid used for research in natural science.

(16) A dry type analysis device for analyzing a component in a body liquid, the dry type analysis device comprising:

an upper member receiving a liquid filter; and a lower member comprising a dry type analysis element, wherein a body liquid is filtered by pressure-reduced filtration so as to obtain a filtered liquid, and the obtained filtered liquid is brought into contact with the dry type analysis element, and wherein the upper member and the lower member are capable of being fitted so as to be substantially air-tight and water-tight when a pressure is reduced.

(17) The dry type analysis device as described in (16) above, which further comprises a seal member in a fitting portion between the upper member and the lower member.

DETAILED DESCRIPTION OF THE INVENTION

Figure 1:
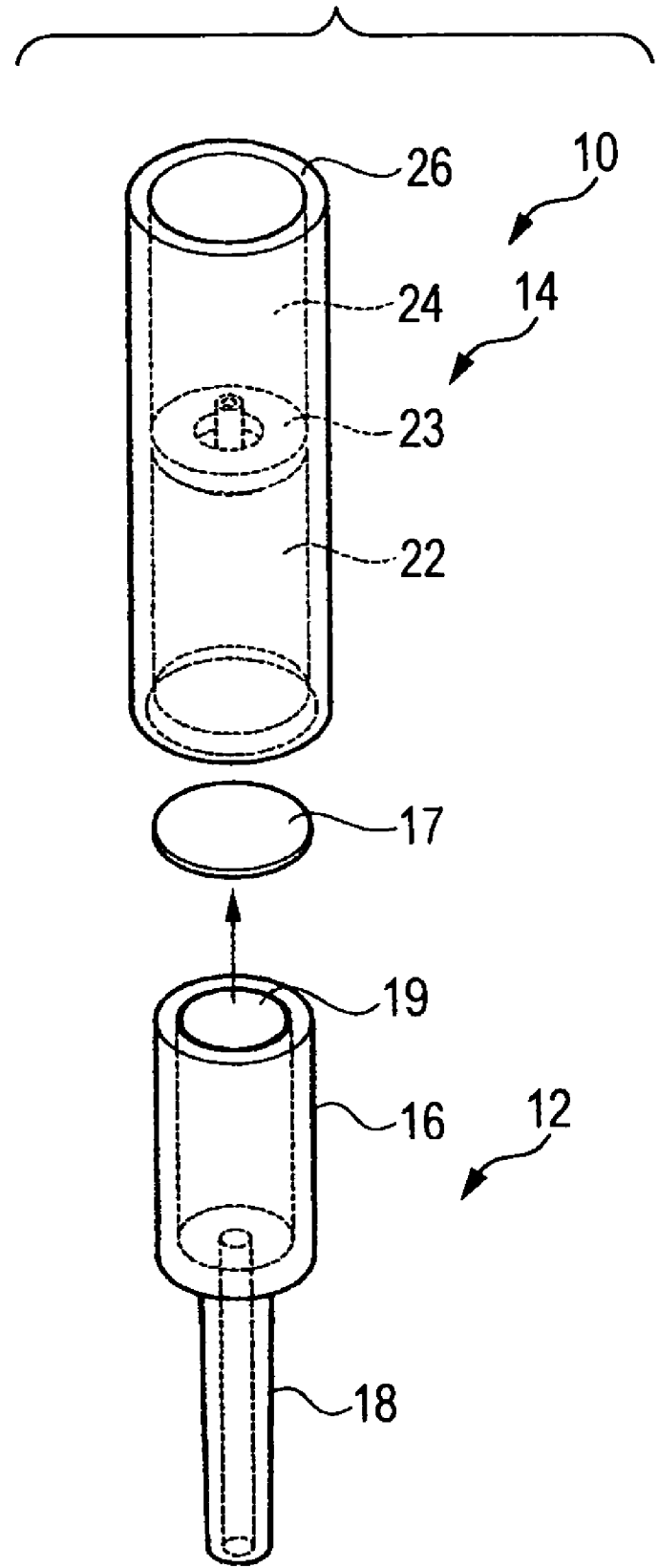
FIG. 1 shows a perspective view showing an embodiment of a liquid filtering instrument according to the present invention.
Figure 2:
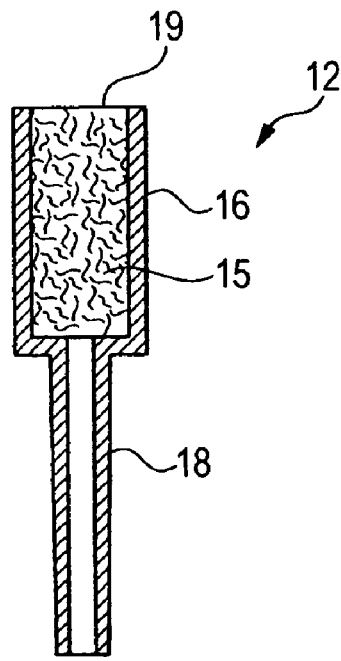
FIG. 2 shows a cross-sectional view showing a filter member 12 according to an embodiment of the present invention.
Figure 3:
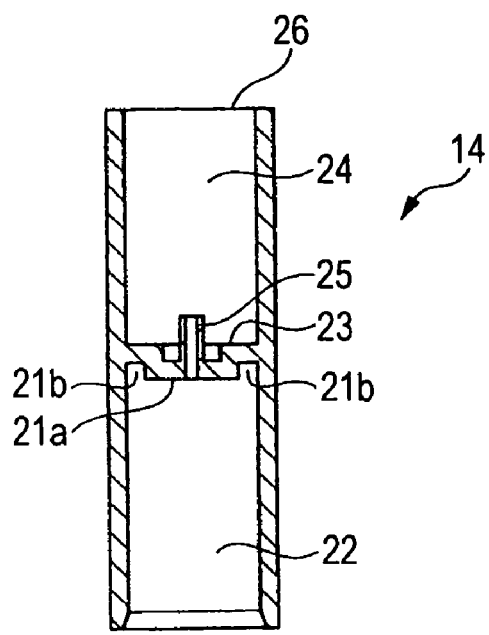
FIG. 3 shows a cross-sectional view showing a holder member 14 according to an embodiment of the present invention.
Figure 4:
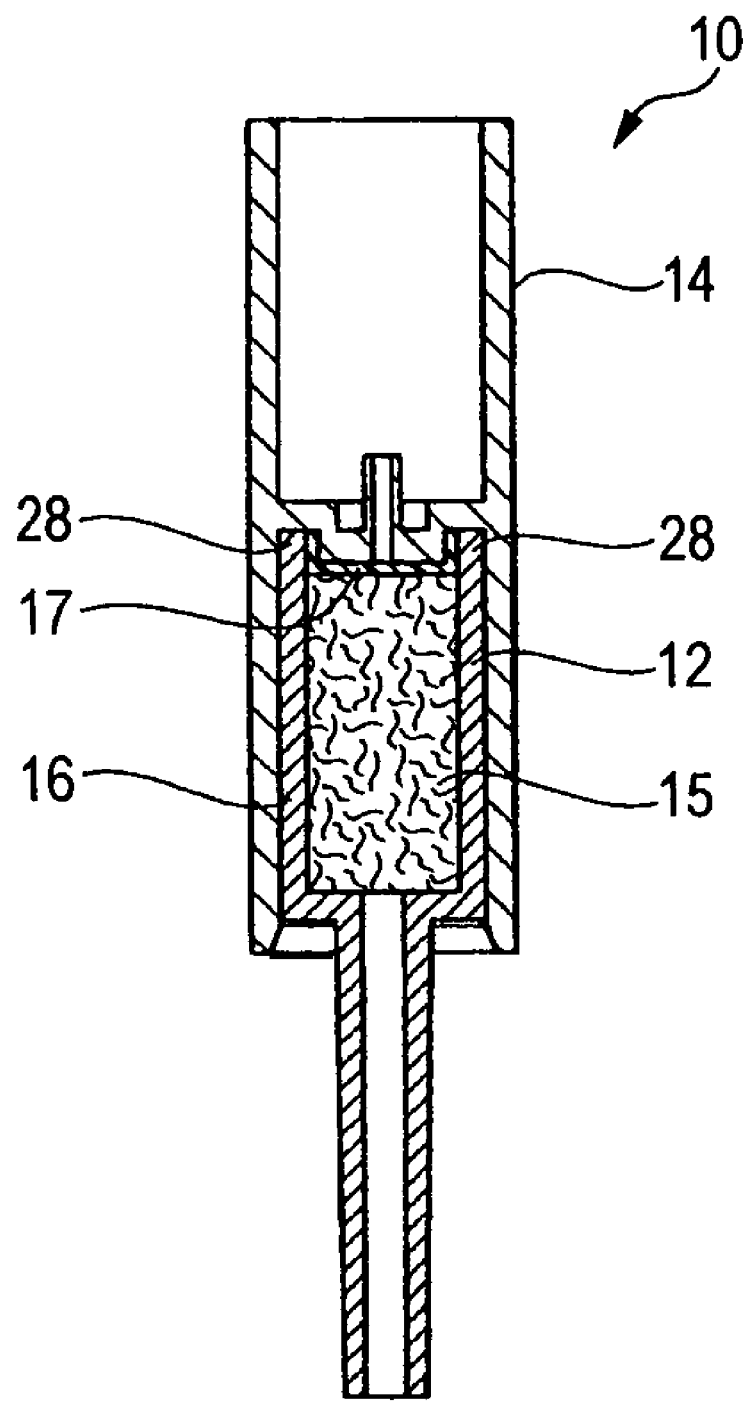
FIG. 4 shows a cross-sectional view showing an embodiment of the liquid filtering instrument according to the present invention.

Embodiments of a liquid filtering instrument according to the present invention will be described in detail with reference to the drawings. FIG. 1 is a perspective view showing an embodiment of the liquid filtering instrument according to the present invention. FIG. 2 and FIG. 3 are cross-sectional views showing a filter member 12 and a holder member 14 constituting the liquid filtering instrument 10 shown in FIG. 1. FIG. 4 is a cross-sectional view showing a liquid filtering instrument 10 having the filter member 12 and holder member 14 being engaged (fitted) with each other.

The liquid filtering instrument 10 shown in FIG. 1 comprises the filter member 12 and the holder member 14 which are designed in a cylindrical shape, and the filter member 12 is engageable with the holder member 14 from the lower side thereof via porous membrane 17 serving as a seal member.

As shown in FIG. 1 and FIG. 2, the filter member 12 has a cylindrical filter accommodating chamber 16 filled with a liquid filter 15. A nozzle 18 for supplying liquid to the filter accommodating chamber 16 is provided at the bottom portion of the filter accommodating chamber 16 so as to extend. When liquid introduced from the nozzle 18 is passed through the liquid filter 15, impurities contained in the liquid are collected by the liquid filter 15. The liquid filter 15 may be formed by laminating plural filtering sheets of glass fiber.

An opening portion 19 for discharging the filtered liquid to the holder member 14 (FIG. 3) side is formed at the upper end (liquid exit side) of the filter accommodating chamber 16.

With respect to the holder member 14, as shown in FIG. 1 and FIG. 3, the inside of the holder member 14 is divided into upper and lower parts by a partition wall 23, and it is partitioned into a filter member accommodating chamber 22 in which the filter member 12 is accommodated and a stocking chamber 24 for stocking filtered liquid of the liquid. The upper end of the stocking chamber 24 is opened to form a suction port 26 which is connected to a suction device (not shown) such as a suction pump or the like.

A cylindrical step 21a projecting downwardly is formed at the center portion of the partition wall 23, and a tubular passage 25 through which the filter member accommodating chamber 22 and the stocking chamber 24 intercommunicate with each other is provided at the center portion of the step 21a so as to extend upwardly. Through this passage 25, the filtered liquid from the filter member 12 enters the stocking chamber 24 and stocked there.

Furthermore, an engaging groove 21b is formed at the peripheral edge portion of the partition wall 23. When the filter member 12 is accommodated in the holder member 14, the liquid filter 15 filled in the filter accommodating chamber 16 is pressed downwardly, and the upper end portion of the side wall of the filter accommodating chamber 16 is engagedly fitted in the engaging groove 21b (FIG. 4).

As shown in FIG. 1 and FIG. 4, it is desirable that the porous membrane 17 serving as the seal member is interposed at the fitting portion (engaging portion) 28 between the upper end portion of the side wall of the filter accommodating chamber 16 and the engaging groove 21b (FIG. 3). By interposing the porous membrane 17 at the fitting portion 28, the porous membrane 17 is sandwiched between the outer peripheral surface of the step 21a and the inner wall surface of the upper end of the filter accommodating chamber 16 so that the cross-section thereof is U-shaped, so that the fitting portion 28 between the filter member accommodating chamber 22 and the filter accommodating chamber 16 is firmly fitted, so that the joint force between the filter member 12 and the holder member 4 can be enhanced.

In addition, by covering the opening portion 19 of the upper end (liquid exit side) of the filter accommodating chamber 16 with the porous membrane 17 as shown in FIG. 4, small-diameter impurities which cannot be collected by the liquid filter 15 can be collected before the filtered liquid enters the passage 25, thereby enhancing the filtering performance.

In order to filter liquid by using the liquid filtering instrument 10 described above, the filter member 12 is first engagedly fitted into the filter member accommodating chamber 22 via the porous membrane 17, and the suction port 26 at the upper end of the holder member 14 is connected to a suction pump (not shown) or the like. The tip of the nozzle 18 is immersed in the liquid, the suction pump is actuated so that the pressure in the liquid filtering instrument 10 is reduced, and the liquid is supplied from the nozzle 18 into the filter accommodating chamber 16. By the reduced-pressure filtration, the liquid is filtered by the liquid filter 15 and the porous membrane 17, and the filtered liquid is stocked in the stocking chamber 24.

According to the liquid filtering instrument 10 of the above embodiment, the pressure is reduced so that the filter member 12 is attracted to the holder member 14, and thus the air-tightness and the water-tightness of the inside of the liquid filtering instrument 10 can be easily maintained by merely engaging the filter member 12 and the holder member 14 with each other. Accordingly, the liquid filtering instrument 10 of this embodiment can omit a joint step such as ultrasonic fusion between the filter member and the holder member or the like which has been hitherto carried out. In addition, the liquid filtering instrument 10 of this embodiment can be a simplified in structure, and it is inexpensive and advantageous for disposable use.

Although the porous membrane 17 is not necessarily needed to maintain air-tightness and water-tightness required for filtration, the joint force at the fitting portion 28 and the filtering performance of the instrument can be enhanced, and thus it is preferable that the porous membrane 17 is interposed at the fitting portion 28 between the filter member 12 and the holder member 14.

The size of the liquid filtering instrument 10 shown in FIG. 1 may be suitable set in accordance with its application. For example, when body liquid such as blood, urine or the like is filtered, the inner diameter of the filter member 12 may be set in the range from 5 mm to 20 mm, and the inner diameter of the holder member 14 may be set in the range from 6 mm to 23 mm. Furthermore, it is preferable that the size of the porous membrane 17 is larger than the inner diameter of the filter member 12.

The materials of the filter member 10 and the holder member 12 are not limited to specific materials, however, they may be formed of materials which are not dissolved by the liquid to be filtered or from which no impurity is eluted. For example, when blood is used as the liquid, material such as transparent polystyrene resin (PS), polypropylene (PP) or the like may be used, and transparent polystyrene resin (PS) is preferably used.

The filter member 12 and the holder member 14 may be manufactured by means such as resin molding or the like.

It is preferable that the liquid filter 15 is formed of fiber of 10 μm or less in diameter. As the fiber that may be used, glass fiber, polyethylene terephthalate (PET) fiber and polyimide fiber can be mentioned. In these materials, glass fiber is preferably used. Soda glass, low alkali glass, borosilicate glass, quartz or the like is used as the material of the glass fiber.

When the liquid to be filtered is blood, it is preferable that glass fiber whose surface is coated with polymer is used. By using glass fiber coated with a polymer, components such as protein or the like contained in blood plasma, which is a filtered liquid, can be suppressed from being adsorbed to the glass fiber. Therefore, no variation occurs in the concentration of the components contained in the blood plasma and the blood plasma of the components can be filtered and withdrawn in a short time at the same level as centrifugal separation.

Polymer having biocompatibility which induces no hemolysis may be used as the polymer to be coated on the surface of the glass fiber. As the polymer which may be used an acrylate-based polymer, polypropylene, polystyrene, nylon, silk, poly(ϵ-caprolactone) or the like can be mentioned. Acrylate-based polymer is preferably used since it is moderately hydrophilic.

Poly(alkoxyacrylate) is preferably used as the acrylate-based polymer. Poly(alkoxyacrylate) can be dissolved in alcohol based organic solvent such as ethanol, methanol or the like when the surface of the glass fiber is treated, and it is easily handled.

As poly(alkoxyacrylate) acrylate-based polymer such as poly methyl methacrylate (PMMA), poly hydroxyethyl methacrylate (PHEMA), poly methoxyethyl acrylate (PMEA) or the like may be specifically used. Out of these materials, PMEA is preferably used.

As a method of coating the surface of the glass fiber with polymer a normal polymer coating method such as dipping, coating, spraying or the like may be used. Specifically, a method of dipping a glass fiber filter sheet in a polymer solution, a method of spraying a polymer solution onto a glass fiber filter sheet or the like may be used. However, the method of dipping the glass fiber filter sheet in the polymer solution is preferable since it can uniformly coat the surface of the glass fiber filter sheet with a polymer.

Furthermore, it is further preferable that the surface of the glass fiber is coated with a polymer after it is cleaned by an acid treatment. By subjecting the glass fiber to the acid treatment, elution of components such as sodium, etc., from the glass fiber can be suppressed. Organic acid is preferably used as the acid for the cleaning treatment for the glass fiber.

With respect to the porous membrane 17, the hole diameter is preferably set to 0.2 μm to 30 μm, further preferably to 0.3 μm to 8 μm, more preferably to 0.5 μm to about 4.5 μm and particularly preferably to 0.5 μm to 3 μm.

Furthermore, it is preferable that the porosity thereof is higher. Specifically, the porosity is preferably set to about 40% to about 95%, more preferably to about 50% to about 95%, and further preferably to about 70% to about 95%.

As the porous membrane 17, cellulosic porous membrane such as nitrocellulose porous membrane, cellulose acetate porous membrane, cellulose propionate porous membrane, regenerated cellulose porous membrane or the like, polysulfone porous membrane, polyether sulfone porous membrane, polypropylene porous membrane, polyethylene porous membrane, polyvinylidene chloride porous membrane, or the like may be used. More preferably, polysulfone porous membrane and polyether sulfone porous membrane can be used.

Furthermore, the surface of the porous membrane 17 may be subjected to a hydrophilic treatment using hydrolysis, hydrophilic polymer, active agent or the like. A method and compounds which are normally used in the hydrophilic treatment may be used as the hydrolysis method, the hydrophilic polymer and the active agent which are applied to the hydrophilic treatment.

The liquid which can be filtered by the liquid filtering instrument of the present invention is not limited to a specific one, and blood, body liquid and urine of humans or other animals, liquid for examining environment-related materials, liquid for examining agriculture, fishery, food products, and liquid used for natural science research can be mentioned. As the liquid for examining the environment-related materials fresh water, sea water or liquid extracted from the soil, etc., as the liquid for examining agriculture, fishery and the foods, agricultural products and liquid extracted from the agricultural products, fishery products and liquid extracted from the fishery products, foods achieved by processing the agricultural products and/or the fishery products and liquid extracted from the foods achieved by processing the agricultural products and/or the fishery products can be mentioned. As the liquid used for natural science research liquid used for research such as chemistry, biology, geoscience, physics, etc., can be mentioned.

Figure 5:
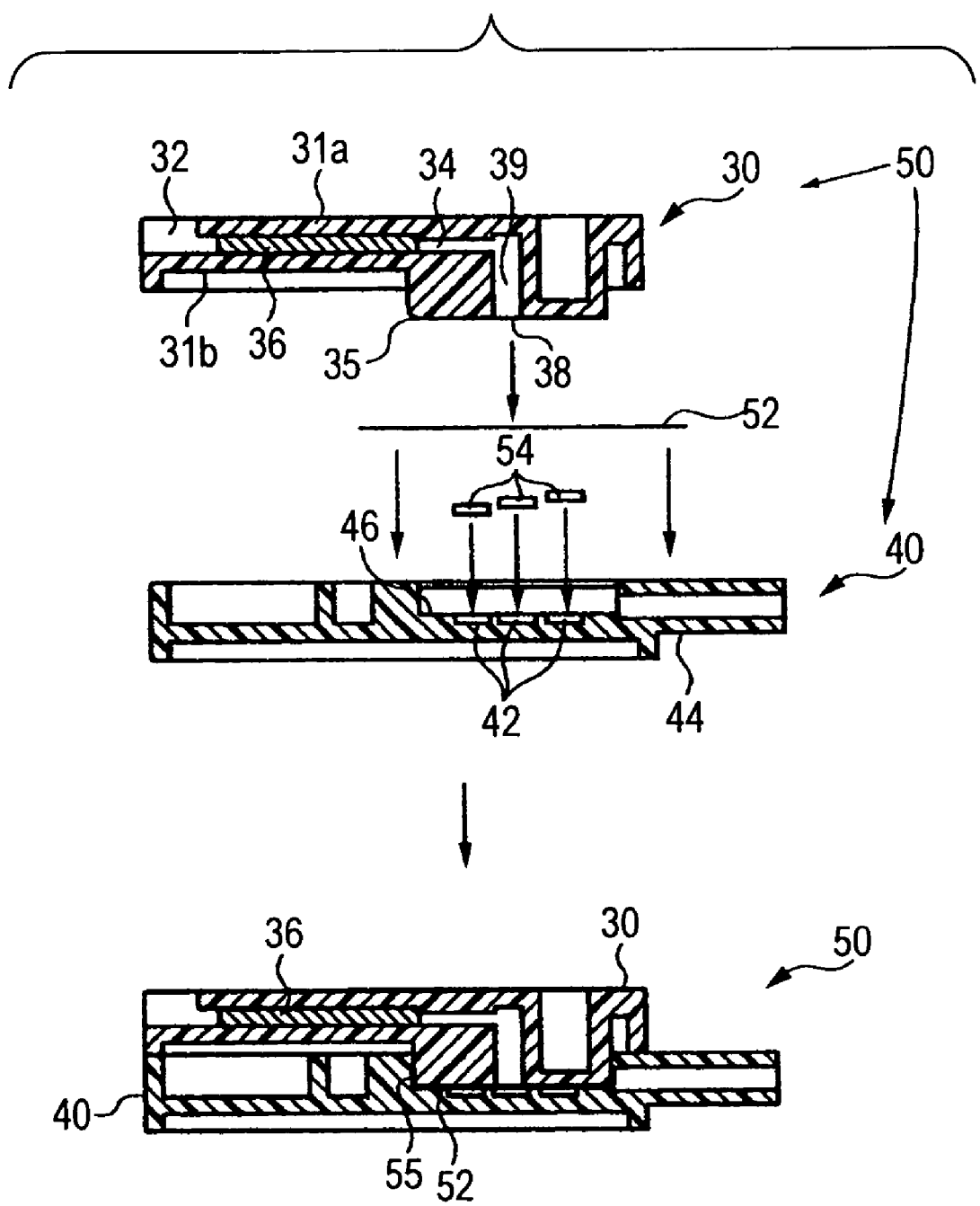
FIG. 5 shows a cross-sectional view showing an embodiment of a dry type analysis device according to the present invention.
Figure 6A:
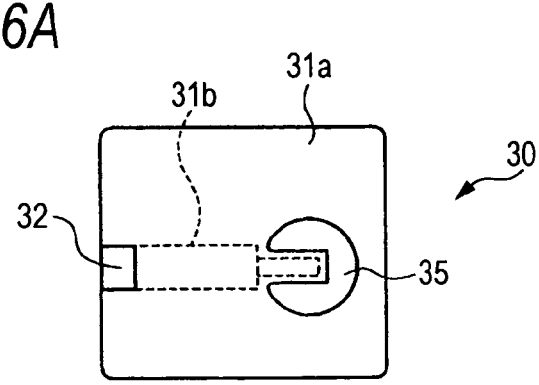
FIG. 6A shows a top view showing an upper member 30.
Figure 6B:
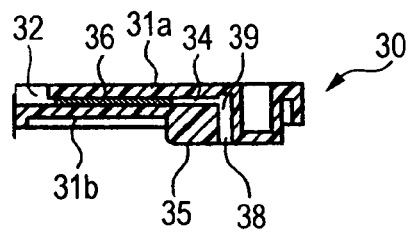
FIG. 6B shows a cross-sectional view showing the upper member 30 according to an embodiment of the present invention.
Figure 7A:
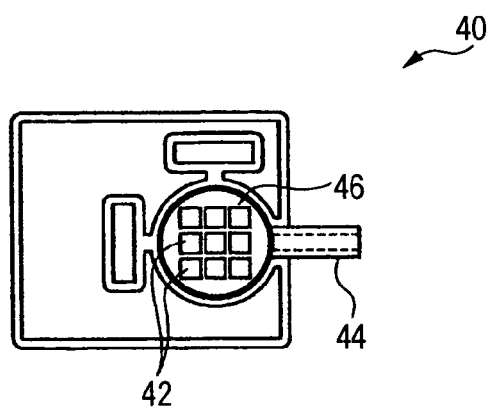
FIG. 7A shows a top view showing a lower member 40.
Figure 7B:
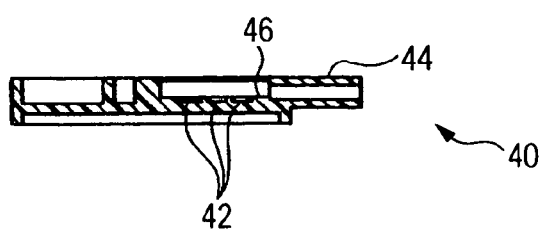
FIG. 7B shows a cross-sectional view of the lower member 40 according to an embodiment of the present invention.

Next, an embodiment of the dry type analysis device according to the present invention will be described. FIG. 5 is a cross-sectional view showing the embodiment of the dry type analysis device according to the present invention. FIG. 6 and FIG. 7 are top views (FIG. 6A, FIG. 7A) and cross-sectional views (FIG. 6B, FIG. 7B) showing an upper member 30 and a lower member 40 constituting a dry type analysis device 50 shown in FIG. 5.

As shown in FIG. 5 to FIG. 7, the dry type analysis device 50 according to the embodiment comprises the upper member 30 and the lower member 40 whose profiles are substantially rectangular parallelepiped, and the upper member 30 is engageable with the lower member 40 via porous membrane 52 (FIG. 5) serving as a seal member.

As shown in FIG. 5 and FIG. 6, a supply port 32 for supplying body liquid is provided at the upper surface side of the upper member 30. The supply port 32 intercommunicates with a flow path 34 formed in the horizontal direction by two large and small wall plates 31a and 31b constituting the upper member 30. The flow path 34 is filled with a liquid filter 36 through which body liquid supplied is filtered.

A short and cylindrical engaging projecting portion 35 is formed at the lower surface side of the upper member 30, and a discharge path 39 intercommunicating with the flow path 34 is disposed at the axis of the cylinder. The filtered liquid fed through the flow path 34 is led downwardly through the discharge path 39, and then fed from the exit 38 of the discharge path 39 to the lower member 40 (FIG. 7).

As shown in FIG. 5 and FIG. 7, the lower member 40 is provided with an engaging recess portion 46 having a circular bottom surface which is engageable with the engaging projecting portion 35.

Cells 42 on which dry type analysis elements 54 are mounted are provided, for example, at nine places in a matrix form on the bottom surface portion of the engaging recess portion 46. Each dry type analysis element 54 makes a reaction such as variation of coloring or the like through the contact thereof with filtered liquid of the body liquid. Furthermore, a suction nozzle 44 to be connected to a suction pump (not shown) or the like is provided on the side wall of the engaging recess portion 46 so as to extend horizontally.

In order to form the dry type analysis device 50 in which the upper member 30 and the lower member 40 are engaged (fitted) with each other, for example, nine dry type analysis elements 54 are first mounted on the cells 42 of the lower member 40 as shown in FIG. 5. The porous membrane 52 which is larger in size than the engaging projecting portion 35 and the engaging recess portion 46 is disposed above the engaging recess portion 46, and the engaging projecting portion 35 is engagedly fitted in the engaging recess portion 46 so as to sandwich the porous membrane 52, thereby forming the dry type analysis device 50 in which the porous membrane 52 is pinched at the fitting portion 55.

In order to analyze body liquid by using the dry type analysis device 50, the upper member 30 and the lower member 40 are engaged with each other as described above, and the suction nozzle 44 is connected to the suction pump (not shown). The body liquid as a test sample (analyte) is supplied from the supply port 32, and the suction pump is actuated to filter the body liquid under reduced pressure. The filtered liquid is brought into contact with the dry type analysis elements 54 facing the exit 38 of the discharge path 39, and coloring variation or the like of the dry type analysis elements 54 is observed to thereby make an analysis. In place of the suction pump, a syringe or the like may be used for the pressure-reduced filtration in the dry type analysis device 50.

According to the dry type analysis device 50 as described above, as in the case of the liquid filtering instrument 10 (FIG. 1), the joint force between the upper member 30 and the lower member 40 can be enhanced under reduced pressure by merely engaging the upper member 30 and the lower member 40 with each other, and sufficient air-tightness and water-tightness can be maintained. Accordingly, the step of joining these members, etc., can be omitted, and an inexpensive dry type analysis device 50 which is simplified in structure can be achieved. The dry type analysis device 50 is also remarkably advantageous for disposable use.

With respect to the porous membrane 52, as in the case of the liquid filtering instrument 10 (FIG. 1), it is not necessarily needed to maintain air-tightness and water-tightness needed for filtration. However, by disposing it at the fitting portion 55 between the upper member 30 and the lower member 40, the joint force at the fitting portion 55 and the filtration performance can be enhanced. Therefore, it is preferable that the porous membrane 52 is interposed in the fitting portion 55 between the upper member 30 and the lower member 40.

It is preferable that the shape and size of the dry type analysis device 50 are set so that it is easily held by hand, however, any shape and any size may be set. Specifically, it is preferably designed in a rectangular shape so that one side of the bottom surface thereof is set to 10 to 50 mm and the thickness thereof is set to 2 to 10 mm. It is preferable that the size of the porous membrane 52 is larger than that of the engaging recess portion 46.

Furthermore, the body liquid which can be analyzed by the dry type analysis device 50 of this embodiment is not limited to a specific one, however, blood, urine, etc., of humans and other animals may be used.

The liquid filter 36 and the porous membrane 52 can be suitably selected in accordance with the body liquid as test sample, and the same materials as used for the liquid filter 15 and the porous membrane 17 in the above-mentioned liquid filtering instrument 10 (FIG. 1) may be used.

A color developing reagent which is frequently used for analysis of body liquid may be used as the dry type an analysis elements 54 mounted in the lower member 40. The color developing reagent is a material which reacts with a test sample component to be measured and produces fluorescence or emits light by photo/electrical/chemical reaction, whereby the test sample component to be measured can be quantitatively or qualitatively analyzed. An example of the color developing reagent usable in the present invention may be Fuji Dri-Chem Mount Slide GLU-P (measurement wavelength; 505 nm, measurement component; glucose) and TBIL-P (measurement wavelength; 540 nm, measurement component; total bilirubin) made by Fujifilm Co., Ltd.

Furthermore, as another color developing reagent materials described in Fujifilm Research Report, No. 40 (Fuji Photo Film Co., Ltd., published in 1995), p. 83, clinical pathology, Extra edition, special topics No. 106, Dry Chemistry/New Development for Simple Examination (The Clinical Pathology Press, published in 1997), etc., may be used.

In place of the color developing reagent, the following may be used as the dry type analysis element 54. That is, an enzymatic electrode achieved by blending and solidifying glucose oxidase (GOD), 1,1'-dimethyl ferrocene and carbon paste formed of the mixture of graphite powder and paraffin is used as an acting electrode, a silver/silver chloride electrode is used as a reference electrode and a platinum electrode is used as a counter electrode, and a current value which increases in accordance with the concentration of glucose in the test sample can be measured. More Specifically, materials described in "Report of Hokkaido Industrial Research Institute", No. 290, pp. 173-177 (1991) by Okuda, Mizutani, Yabuki, et al. can be mentioned.

The style of the dry type analysis element 54 is preferably designed in a film shape, and it may be as a single layer or multi-layer.

Any material may be used for the upper member 30 and the lower member 40 as long as it is not eroded by the body liquid, and the test sample can be passed through the material efficiently. Specifically, resin such as rubber, plastic or the like and silicon-contained material may be used.

As the plastic or rubber, polymethylmethacrylate (PMMA), polycyclic olefin (PCO), polycarbonate (PC), polystyrene (PS), polyethylene (PE), polyethyleneterephthalate (PET) polypropylene (PP), polydimethyl siloxane (PDMS), natural rubber, synthetic rubber and derivatives thereof may be used. As the silicon-contained material, glass, quartz, amorphous silicon such as silicon wafer or the like, silicone such as polymethyl siloxane or the like may be used. Out of these materials, PMMA, PCO, PS, PC, glass and silicon wafer are preferable.

With respect to the paths (FIG. 5) for the body liquid and the filtered liquid, such as the flow path 34, the discharge path 39, etc., it is preferable that at least one of the width, depth and length thereof is equal to 1 mm or more. If the flow path 34 and the discharge path 39 satisfy the above condition, the test sample can efficiently go through these paths.

Any shape may be adopted for the flow path 34, the discharge path 39, etc., as long as the test sample can pass therethrough. Furthermore, each path may be designed as a single path or designed to be branched into two or more paths. Furthermore, it may be designed in a linear shape, a curved shape or the like, and it is preferably designed in a linear shape.

The respective parts such as the supply port 32, the flow path 34, the discharge path 39, the cells 42, etc., which are formed in the upper member 30 and the lower member 40 can be formed on a solid board by the micro-fabrication technology.

As the micro-fabrication technology of forming these parts, a method described in "Micro-reactor—Synthesis Technology for New Age—(published in 2003 by C.M.C. under the editorship of Junichi Yoshida, Professor of Graduate School of Kyoto University, Engineering Research Department), "Micro-fabrication Technology, Applied edition—Application to Photonics/Electronics/Mechatronics— (published in 2003 by NTS, edited by Event Committee of Society of Polymer Science, Japan), etc., may be used.

As representative methods, an LIGA technology using X-ray lithography, a high aspect ratio photolithography method using EPON SU-8, a micro electric discharging method (μ-EDM), a silicon high aspect ratio processing method based on Deep RIE, a Hot Emboss processing method, a laser beam lithography, a laser processing method, an ion beam machining method, a mechanical micro cutting method using a micro-tool formed of a hard material such as diamond or the like, etc., may be used. These technologies may be used alone or in combination. As a preferable micro-fabrication technology, the LIGA technology using the X-ray lithography, the high aspect ratio photolithography method using EPON SU-8, the micro electric discharging method (μ-EDM) and the mechanical micro cutting method are used.

The respective parts of the dry type analysis device 50 may be formed as follows. That is, a pattern which is formed on a silicon wafer by using a photoresist is used as a mold, and resin is poured into the mold and solidified (molding method). In the molding method, silicon resin which is represented by PDMS or the derivatives thereof may be used.

It is desired that the surfaces of the flow path 34, the discharge path 39, etc., are treated or modified as occasion demands so that test sample, particularly whole blood or blood plasma can quickly pass therethrough. The surface treating or modifying method is varied in accordance with the material constituting the flow paths, and an existing method may be used. For example, a plasma treatment, a glow treatment, a corona treatment, a method of using a surface treatment agent such as a silane coupling agent or the like, a method of carrying out a surface treatment by using poly hydroxyethyl methacrylate (PHEMA), poly methoxyethyl acrylate (PMEA) and acrylic polymer can be mentioned.

The dry type analysis device 50 may be mounted on a blood collecting device and used as a blood collecting unit. The dry type analysis device 50 is mounted on the blood collecting device and assembled freely slidably while maintaining a substantially air-tight state, whereby a hermetic space can be formed inside so that the pressure of the hermetic space can be reduced.

Figure 8:
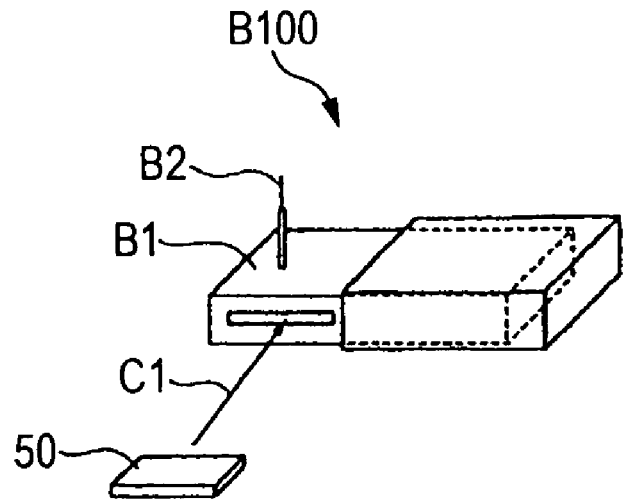
FIG. 8 shows a schematic diagram showing a blood collecting unit according to an embodiment of the present invention.
Figure 9:
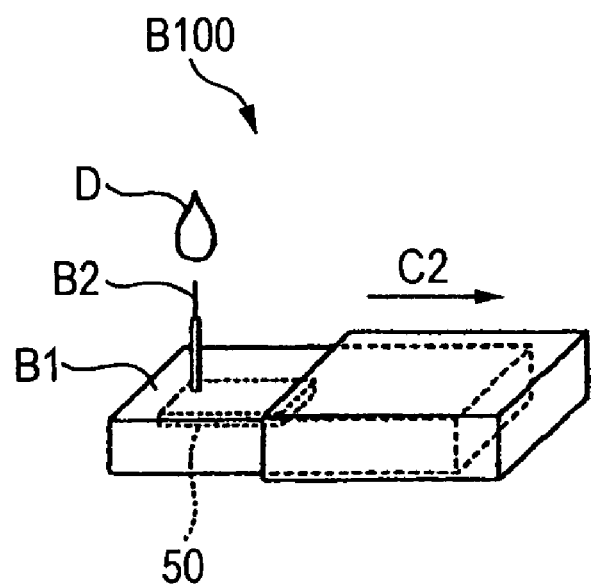
FIG. 9 shows a schematic diagram showing the blood collecting unit according to an embodiment of the present invention.

A preferable example of the blood collecting unit will be described with reference to FIG. 8 and FIG. 9, however, the present invention is not limited to this embodiment.

The dry type analysis device 50 is mounted in a blood collecting device B1 from the direction C1 to thereby assemble a blood collection unit B100. After the mounting, a puncture needle B2 is pierced into a human or animal to collect the whole blood D. As described above, a part of the blood collecting device is slid in the direction C2 to reduce the pressure in the blood collecting device, so that the whole blood D thus collected enters a flow path A1 of the dry type analysis device 50 and further is led to a portion A2 having color developing reagent carried thereon to react with the color developing reagent. After the reaction, the dry type analysis device 50 can be detached from the blood collecting device B1, and supplied for detection. The dry type analysis device 50 may be detached from the blood collecting device B1 in the direction C1, that is, detached to the far side of the blood collecting device B1 in the same direction as when it is mounted, or it may be detached in the opposite direction to the direction C1, that is, from the same side as when it is mounted.

Furthermore, when the tip of a finger, an elbow, a heel or the like is punctured by a lancet or the like to extract peripheral blood and the peripheral blood thus extracted is used for examination, no puncture needle is required to the blood collecting device of the blood collecting unit. Any structure may be used for the blood collecting unit as long as it has a hollow structure and a function of leading blood to the dry type analysis device 50.

Any shape and any size may be adopted for the blood collecting unit as long as the dry type analysis device 50 can be mounted in the blood collecting device, it can be freely slidably assembled while maintaining a substantially air-tight state and a hermetic space can be formed so that the inside thereof can be reduced in pressure. It is preferable that it is designed to be easily held by hand and operated.

By forming the hermetic space so that the inside thereof can be reduced in pressure, the collected whole blood can be put into the flow path 34 of the dry type analysis device 50 and quickly led to the dry type analysis elements 54.

Figure 10:
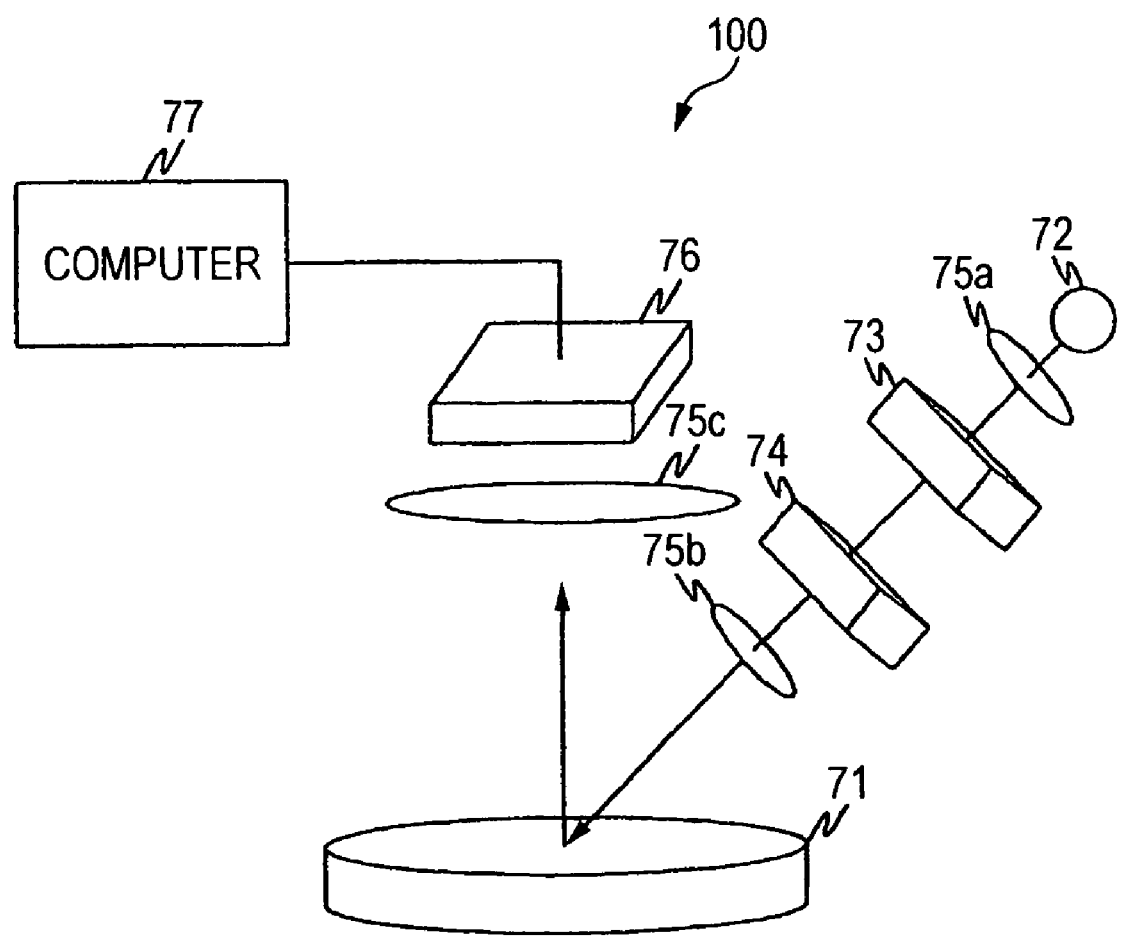
FIG. 10 shows a schematic diagram showing a measuring device according to an embodiment of the present invention.

A measuring device for analyzing the dry type analysis device 50 according to this embodiment will be described. FIG. 10 is a schematic diagram showing an example of the measuring device for analyzing the dry type analysis device 50 (FIG. 5).

As shown in FIG. 10, the measuring device 100 is equipped with a set-up unit 71 on which a test sample serving as a measurement target is mounted. The dry type analysis device 50 is mounted on the set-up unit 71. An object to be actually supplied for measurement is a portion of the dry type analysis element 54 (FIG. 5) which has reacted with the test sample of the dry type analysis device 50.

Furthermore, the measuring device 100 is equipped with a light source 72 using a light emitting device such as a halogen lamp or the like for irradiating light to the test sample, a light varying unit 73 for varying the intensity of light irradiated from the light source 72, a wavelength varying unit 74 for varying the wavelength of light irradiated from the light source 72, lenses 75a and 75b for collimating and converging light irradiated from the light source 72, a lens 75c for converging reflected light from the test sample, an area sensor 76 serving as a photodetecting element for photodetecting the reflected light converged by the lens 75c, and a computer 77 for controlling the respective parts, achieving a measurement result in connection with the state of the light varying unit 73 and the light amount of light detected by the area sensor 76 and outputting the measurement result to a display or the like. In this case, the computer 77 controls the respective parts, however, a computer for collectively controlling the respective parts may be separately prepared.

With respect to the light varying unit 73, a perforated plate of a metal mesh formed of stainless steel and a dimmer filter such as an ND filter or the like are mechanically inserted into and out between the light source 72 and the test sample to vary the intensity of light irradiated from the light source 72 to the test sample. At the initialization, the dimmer filter is maintained to be inserted between the light source 72 and the test sample. In the following description, the metal mesh is assumed to be a stainless mesh. Furthermore, the perforated stainless mesh plate and the dimmer filter such as an ND filter or the like may be manually inserted into and out.

With respect to the wavelength varying unit 74, some of the plural kinds of interference filters are mechanically inserted into and out between the light source 72 and the test sample to vary the wavelength of light irradiated from the light source 72 to the test sample. In this embodiment, the wavelength varying unit 74 is disposed between the light varying unit 73 and the set-up unit 71, however, it may be disposed between the light source 72 and the light varying unit 73. Furthermore, the plural kinds of interference filters may be manually inserted into and out.

The area sensor 76 is a solid-state image sensing device such as a CCD or the like. When the dry type analysis element 54 (FIG. 5) of the dry type analysis device 50 mounted on the set-up unit 71 reacts with the test sample such as blood or the like, light is irradiated from the light source 72 to the reactant and reflection light is reflected from the reactant, the area sensor 76 detects the reflection light from the reactant, converts the light thus detected into an electrical signal and then outputs the electrical signal to the computer 77. The area sensor 76 can detect the light reflected from the dry type analysis element 54 on a plane basis. Therefore, the area of each reagent can be simultaneously measured, that is, the measurement can be performed for plural items at the same time.

The computer 77 converts the electrical signal corresponding to the detected light amount output from the area sensor 76 to an optical concentration value on the basis of the data of an analytical curve stored in a built-in memory or the like, calculates the content amount or the like of various kinds of components contained in the test sample from the optical concentration value and outputs the calculation result to the display or the like. When plural items are measured, the computer 77 extracts the electrical signal corresponding to the detected light amount output from the area sensor 76 for every plural areas of the dry type analysis elements, and determines the content amounts of the components contained in the test sample by every plural areas. Furthermore, the computer 77 controls the light varying unit 73 and the wavelength varying unit 74 in accordance with the amount of reflected light from the test sample which is detected by the area sensor 76 and the type of reagent to be reacted with the test sample so that the light amount of light from the light source 72 is varied or the wavelength thereof is varied.

In the measuring device 100 thus constructed, when the amount of reflected light from the test sample is small to the extent that it does not enter the dynamic range of the area sensor 76, the light varying unit 73 removes the stainless mesh plate or the ND filter from the area between the light source 72 and the test sample to increase the intensity of light irradiated from the light source 72. Accordingly, the amount of reflected light from the test sample is increased, and the reflected light amount enters the dynamic range of the area sensor 76. Therefore, even when the dynamic range of the area sensor 76 is narrow, the reflected light can be detected with high precision, and thus the measurement precision of the content amounts of the components contained in the test sample can be enhanced.

In this embodiment, light is irradiated from the light source 72 to the test sample, and the content amount of each component contained in the test sample is determined on the basis of the reflected light. However, the content amount of each component contained in the test sample may be determined on the basis of light transmitted through the test sample.

Furthermore, in this embodiment, the reflected light from the test sample is detected by using the area sensor such as a CCD or the like. However, the present invention is not limited to the area sensor, and a line sensor may be used.

As a CCD used in this embodiment, preferably used is a so-called honeycomb type CCD in which photodetectors such as photodiodes or the like are arranged in the longitudinal and lateral directions at predetermined intervals on a semiconductor substrate, and the photodetectors contained in the adjacent photodetector arrays are arranged so as to be displaced from one another at about half of the pitch of the photodetectors in each photodetector array in the column direction.

In the foregoing description, the measuring device 100 varies the light intensity in accordance with the amount of reflected light from the test sample on a real-time basis. However, in accordance with a measurement target component contained in the test sample, the content amount of the measurement target component may be measured according to a preset sequence. The operation in this case will be described below.

When the dry type analysis device is mounted in the set-up unit 71 and a measurement item is set, the measuring device 100 starts a measurement according to the pattern corresponding to the measurement item thus set. First, the computer 77 selects a light intensity for the measurement from plural kinds of intensities, and irradiates light having the selected light intensity to the test sample. When the area sensor 6 detects light reflected from the test sample, the computer 7 outputs the measurement result corresponding to the light amount of reflected light detected by the area sensor 6 and the selected light intensity. Through this series of operations, the measurement of a measurement target component contained in the test sample can be performed with high precision.

In a case where the exposure time of the CCD is varied without varying the light intensity, when the dry type analysis device is mounted in the set-up unit 71 and a measurement item is set, the measuring device 100 starts a measurement according to the pattern corresponding to the measurement item thus set. First, the computer 77 irradiates light to the test sample. The area sensor 76 detects light reflected from the test sample for an exposure time selected from plural kinds of exposure times by the computer 77. Finally, the computer 77 outputs the measurement result corresponding to the light amount of reflected light detected by the area sensor 6 and the selected exposure time. Through this series of operations, the measurement of a measurement target component contained in the test sample can be performed with high precision.

The measuring device 100 is not limited to the embodiment in which light is irradiated from the light source 72 to the dry type analysis elements and the content amount of the component contained in the test sample is determined on the basis of reflected light or transmitted light. For example, the content amount of the component contained in the test sample may be determined by detecting light such as fluorescence or the like emitted from the dry type analysis elements when light is irradiated from the light source 72 to the dry type analysis elements. Furthermore, the content amount of a component contained in the test sample may be determined by perfectly intercepting light from the light source 72 with the light varying unit 3 or using no light source 72 to thereby maintain the dry type analysis elements under a light unexposed state, and detecting light based on light emission such as chemiluminescence or the like emitted from the dry type analysis elements.

The present invention is not limited to the above embodiments, and the materials, shapes, dimensions, styles, numbers and arrangement positions of the liquid filtering instrument 10, the filter member 12, the holder member 14, the liquid filters 15 and 36, the porous membrane 17 and 52, the dry type analysis device 50, the upper member 30, the lower member 40, the dry type analysis elements 54, etc., can be suitably modified.

EXAMPLES

Examples of the present invention will be described hereunder, however, the present invention is not limited to these examples.

Example 1

Example of Liquid Filtering Instrument

1. Manufacture of Liquid Filtering Instrument

Manufacturing Example 1

The liquid filtering instrument shown in FIG. 1 was manufactured. The filter member 12 and the holder member 14 were formed of transparent polystyrene resin (PS). The inner diameter of the filter member 12 was set to about 8 mm, the outer diameter of the filter member 12 was set to about 11 mm, the inner diameter of the holder member 14 was set to about 11 mm and the outer diameter of the holder member 14 was set to about 12 mm.

Glass fiber filter paper (made by Whatman plc.; GF/D) which was made at a thickness of about 1 mm was punched out at a diameter of 8 mm into sixteen pieces of glass fiber filter paper, the sixteen pieces of the glass fiber filter paper were filled in the filter accommodating chamber 16 of the filter member 12 as liquid filter 15.

Polysulfone porous membrane (made by Fujifilm Co., Ltd.) used in Fuji Dri-Chem Plasma filter PF was punched out at a diameter of 11 mm, and punched-out porous membrane thus achieved was used as the porous membrane 17.

Manufacturing Example 2

The liquid filtering instrument 10 (FIG. 1) was manufactured in the same manner as described above except that the liquid filter used in the manufacturing example 1 was changed to acetic-acid-treated glass fiber filter paper, PMEA (poly (methoxyethyl acrylate))-treated glass fiber filter paper or glass fiber filter paper which was subjected to the acetic-acid treatment and the PMEA-treatment. The acetic acid treatment and the PMEA treatment were carried out according to the following procedures of (A) to (C).

(A) Acetic Acid Treatment

Glass fiber filter paper which was made at a thickness of about 1 mm (made by Whatman plc.; GF/D) was cut into sheets of about 200 mm in longitudinal direction and about 150 mm in the lateral direction, and three sheets thus achieved were stacked and put in a stainless steel vat. Acetic acid of 1 mL was dissolved in ion-exchange water of 999 g to prepare acetic acid water solution of about 16.5 mM in concentration. 200 mL of acetic acid water solution thus prepared was gently poured into the vat to immerse the glass fiber filter paper in the acetic acid water solution. The vat was swayed for 30 seconds to permeate the acetic acid water solution into the papers, and then kept stationary for 4 minutes and 30 seconds. Thereafter, the vat was tilted for 30 seconds to remove the liquid. The operation of immersing the sheets in the acetic acid water solution was carried out again, and the treatment using the acetic acid water solution was carried out totally twice.

Subsequently, 200 mL of ion-exchange water was gently poured into the vat to immerse the glass fiber filter paper in the ion-exchange water, the vat was swayed for 30 seconds to permeate the liquid into the glass fiber filter paper, and then inclined for 30 seconds to remove the liquid. The operation of immersing the glass fiber filter paper in the ion-exchange water was further carried out four times, and the treatment based on the ion-exchange water was carried out a total of five times. Subsequently, 200 mL of methanol was gently poured into the vat to immerse the glass fiber filter paper in the methanol, and the vat was swayed for 30 seconds to permeate the liquid into the glass fiber filter paper, and then inclined for 30 seconds to remove the liquid. Subsequently, the glass fiber filter paper was taken out while pinched by forceps, and the glass fiber filter paper thus taken out was gently placed on a portion at which a Kimtowel made by Crecia Co., Ltd. was laid and then a Kimwipe made by Crecia Co., Ltd. was laid, the Kimtowel and the Kimwipe being prepared in a draft in advance. Furthermore, the glass fiber filter paper was dried for 1.5 to 3 hours at room temperature while the air in the draft was suctioned.

(B) PMEA (Poly(Methoxyethyl Acrylate)) Treatment

As in the case of the acetic acid treatment, a Glass fiber filter sheet which was made at a thickness of about 1 mm (made by Whatman plc.; GF/D) was cut into sheets of about 200 mm in longitudinal direction and about 150 mm in the lateral direction, and three sheets thus achieved were stacked and placed in a stainless steel vat. 1 mL of toluene solution containing about 20% of PMEA (made by Scientific Polymer Products Company; molecular weight of PMEA is about 100,000) was diluted with methanol of 199 mL to achieve a PMEA solution of about 0.1% in concentration, and the PMEA solution thus achieved was gently poured into the vat to immerse the glass fiber filter paper in the PMEA solution. The vat was swayed for 30 seconds to permeate the liquid into the glass fiber filter paper, and then kept stationary for 4 minutes and 30 seconds. Thereafter, the vat was inclined for 30 seconds to remove the liquid. Subsequently, the glass fiber filter paper was pinched by forceps and gently taken out, and gently placed on a portion at which a Kimtowel was laid and further a Kimwipe was laid, the Kimtowel and the Kimwipe being prepared in a draft in advance. Therefore, the glass fiber filter paper was dried at room temperature for 1.5 to 3 hours while the air in the draft was suctioned.

(C) Vacuum Drying

The glass fiber filter paper which was subjected to the acetic acid treatment or the PMEA treatment was put on the portion at which the Kimtowel was laid and further the Kimwipe was laid on the Kimtowel. Under this state, the glass fiber filter paper was put in a vacuum drying machine and dried under reduced pressure of about 0.01 to 10 mPa at room temperature for 15 to 21 hours. After the drying was finished, it was left under the atmosphere of the laboratory (20 to 30° C., about 30 to 70% RH) for 3 hours or more, and stored while placed in a vinyl bag.

2. Filtering Result Based on Liquid Filtering Instrument

Blood was collected from a normal healthy male by using a blood collecting vessel using heparin lithium as an anticoagulant. The hematocrit of the whole blood thus achieved was equal to H46%. The whole blood was put in a cleaning test tube Larbo made by Terumo Corporation (15.5 mm in diameter, 100 mm in length) was cut at a length of about 30 mm to achieve a glass test tube, and the whole blood was put in the glass test tube thus achieved. A lid of Teflon (trademark) mixed silicon material whose inner diameter was tapered from 8 mm to 20 mm in diameter was formed. A hole was formed at the upper end of this lid, and it was connected to a pressure control type pump suction machine through a tube so that the glass test tube is maintained air-tight.

The filter member 12 and the holder member 14 which were formed in the (manufacturing example 1) and the (manufacturing example 2) were engaged with each other while the porous membrane was sandwiched therebetween, and the lid formed as described above was secured to the opening portion 26 of the upper end of the holder member 14. The nozzle 18 of the filter member 12 was immersed in the whole blood, and the pressure control type pump suction machine was actuated to withdraw blood plasma from the whole blood by pressure-reduced filtration. The suction sequence was set as follows. That is, the pressure reducing degree was continuously increased so that the pressure which was 0 mmHg at the suction start time was reduced to −60 mmHg in 30 seconds, further continuously increased so that the pressure was reduced to −130 mmHg in the next 10 seconds, and then the pressure reducing degree of −130 mmHg was maintained until the pump is stopped.

As a result, 140 µL of blood plasma was achieved from 1 mL of the whole blood in total suction time of 200 seconds without leakage of erythrocyte or the like. This result indicated the same filtering performance as a result achieved when 350 µl was achieved from 3 ml of the whole blood by using a Fuji Dri-Chem Plasma Filter PF corresponding to a liquid filtering instrument in which the filter member and the holder member were joined to each other by ultrasonic fusion. Accordingly, it is clear that liquid can be filtered by the liquid filtering instrument of the present invention.

3. Comparison of Materials Used for Liquid Filter

The blood plasma components achieved by the liquid filtering instrument were analyzed by using a clinical examination automatic analyzing device 7170 made by Hitachi, Ltd., and the difference among the liquid filters being used considered. For comparison, the components of blood plasma achieved by carrying out centrifugal separation for 10 minutes at a rotational number of 300 rpm were quantitatively measured.

It has been found that when non-treated glass fiber filter paper was used as the liquid filter 15 (FIG. 1), components such as sodium (Na), potassium (K), chloride ion (Cl), etc., were eluted from glass into blood plasma, and components in the blood plasma such as total cholesterol (TCHO), etc., were adsorbed to the glass fiber filter paper. However, hemolysis was not visually observed, and even when slight hemolysis occurs, it does not obstruct the analysis of the blood plasma.

It has been found that when acetic-acid-treated glass fiber filer paper is used, components such as sodium, potassium, chloride ion, etc., can be prevented from being eluted from glass, and when the PMEA-treated glass fiber filter paper is used, components such as total cholesterol, etc., in blood plasma can be prevented from being adsorbed to the glass fiber filter paper.

Furthermore, it has been found that when the glass fiber filter paper which is subjected to the acetic acid treatment and then the PMEA treatment is used, substantially the same level of blood plasma as the centrifugal-separated blood plasma can be achieved. Furthermore, the blood plasma thus achieved is not red-colored, and as compared with the blood plasma achieved by centrifugal separation, it has been found that the values of potassium (K) and lactate dehydrogenase (LDH) are not large and no hemolysis occurs.

Accordingly, it has been found that hemolysis rarely occurs in the glass fiber filter paper which is subjected to the acid treatment, the PMEA treatment or the PMEA treatment after the acid treatment, and blood plasma which is very suitable for analysis can be achieved. The above result is summarized in Tables 1 to 3.

TABLE 1

Level of blood filtration

Liquid filter used

| Level 1 | No (centrifugal separation) |
| Level 2 | No-treated glass fiber filter paper |
| Level 3 | Acetic-acid-treated glass fiber filter paper |
| Level 4 | PMEA-treated glass fiber filter paper |
| Level 5 | Acetic-acid-treated and then PMEA-treated glass fiber filter paper |

TABLE 2

Component value of blood plasma in each level

| Item | Unit | Level 1 | Level 2 | Level 3 | Level 4 | Level 5 |
|---|---|---|---|---|---|---|
| Na | [meq] | 140.1 | 143.6 | 139.5 | 143.1 | 139.6 |
| K | [meq] | 3.94 | 3.87 | 3.59 | 3.82 | 3.68 |
| Cl | [meq] | 106.6 | 110.0 | 107.5 | 109 | 107.3 |
| Ca | [mg/dL] | 8.66 | 8.78 | 8.73 | 8.84 | 8.67 |
| Total protein (TP) | [g/dL] | 7.00 | 6.78 | 6.85 | 6.83 | 6.92 |
| Total cholesterol (TCHO) | [mg/dL] | 154 | 152 | 154 | 151 | 154 |
| Albumin (ALB) | [g/dL] | 4.03 | 4.08 | 4.05 | 4.05 | 4.06 |
| Lactate dehydrogenase (LDH) | [U/L] | 165 | 172 | 173 | 172 | 171 |

TABLE 3

Difference between the component value of blood plasma and the component value of centrifugal-separated blood plasma in each level

| Item | Unit | Level 1 | Level 2 | Level 3 | Level 4 | Level 5 |
|---|---|---|---|---|---|---|
| Na | [meq] | 0 | +3.5 | −0.6 | +3.0 | −0.5 |
| K | [meq] | 0 | −0.07 | −0.35 | −0.12 | −0.26 |
| Cl | [meq] | 0 | +3.4 | +0.9 | +2.4 | +0.7 |
| Ca | [mg/dL] | 0 | +0.12 | +0.07 | +0.18 | +0.01 |
| Total protein (TP) | [g/dL] | 0 | −0.22 | +0.02 | −0.17 | −0.08 |
| Total cholesterol (TCHO) | [mg/dL] | 0 | −2 | 0 | −3 | 0 |
| Albumin (ALB) | [g/dL] | 0 | +0.05 | +0.02 | +0.02 | +0.03 |
| Lactate dehydrogenase (LDH) | [U/L] | 0 | +7 | +8 | +7 | +6 |

Example 2

Example of Dry Type Analysis Device

1. Manufacturing Example of Dry Type Analysis Device

The upper member 30 and the lower member 40 shown in FIG. 5 were engaged with each other via the porous membrane 52 according to the following procedure to manufacture the dry type analysis device 50.

The upper member 30 and the lower member 40 which were formed of transparent polystyrene at a size of about 24 mm×28 mm were prepared. The engaging projecting portion 35 and the engaging recess portion 46 were designed to have a diameter of about 9 mm. Glass fiber filter paper (made by Whatman plc.; GF/D) for capturing erythrocyte/extracting blood plasma was filled as the liquid filter 36 in the flow path 34.

Furthermore, Fuji Dri-Chem mount slide GLU-P and TBIL-P (made by Fuji Photo Film Co., Ltd.) each of which is cut out to be slightly less than 2 mm in width and slightly less than 2 mm in length were prepared as dry type analysis elements 54, and disposed on nine cells 42 of the lower member 40. Out of the nine cells 42, a total of five GLU-P were filled at the center and four corners, and a total of four TBIL-P were filled at other places.

Subsequently, a square piece of about 18 mm in each side length of polysulfone porous membrane (made by Fuji Photo Film Co., Ltd.) was prepared as the porous membrane 52. The polysulfone porous membrane was gently placed above the engaging recess portion 46, and the upper member 30 and the lower member 40 were engaged with each other while the polysulfone porous membrane was sandwiched between the fitting portion of the engaging projecting portion 35 and the engaging recess portion 46.

2. Setting of Measuring Device

In order to measure the dry type analysis device 50, the measuring device 100 shown in FIG. 10 was prepared. The setting of each member was as follows.

Measuring device 100: inverted stereomicroscope

The following two magnifications at the CCD photodetecting portion were prepared.

0.33 time; 33 μm/pixel at CCD portion 1 time; 10 μm/pixel at CCD portion

Light source 72; Lumina Ace LA-150UX made by Hayashi Watch Works Co., Ltd.

Wavelength varying unit 74 (Interference filter); monochromatic at each of 625 nm, 540 nm, 505 nm Light varying unit 73 (dimmer filter); glass filter ND-25 made by HOYA Co., Ltd. and a homemade filter achieved by perforating a stainless steel plate Area sensor 76 (CCD); 8-bit monochrome camera module XC-7500 made by SONY Corporation Computer 77 (data processing (image processing)); image processing device LUZEX-SE made by Nireco Corporation Means of correcting the reflective optical density; the following six kinds of standard density plates (ceramic specification) made by Fuji Photo Equipment Co., Ltd. were prepared.

Standard density plate; A00 (reflective optical density to 0.05),

A05 (ditto 0.5),

A10 (ditto 1.0),

A15 (ditto 1.5),

A20 (ditto 2.0),

A30 (ditto 3.0)

3. Analysis Based on Dry Type Analysis Device

200 μL of plainly-collected whole blood was poured into the supply port 32 of the dry type analysis device 50 manufactured as described above, and kept stationary for 10 to 20 seconds to develop the whole blood in a glass fiber filter paper (liquid filter 36). Thereafter, the silicon tube was connected to the suction nozzle 44 and a disposable syringe (made by Terumo Corporation) was mounted at the tip of the tube, and the piston of the syringe was gently pulled for suction.

The blood plasma extracted through the filtration is passed through the polysulfone porous membrane, and dropped onto a Dri-Chem mount slide. GLU-P and TBIL-P slide gradually started coloring. The time needed to extract the blood plasma after the whole blood was injected and drop it onto the mount slide was 30 seconds.

The images of the aspect of the coloring of the GLU-P and TBIL-P slide were picked up by using a CCD camera simultaneously with the measurement of the measuring device 100 shown in FIG. 10, and the images thus achieved were processed by using LUZEX-SE. The average detected light amount in the vicinity of the center of the image of the GLU-P located at the center of the cell 42 and the TBIL-P slide located adjacent to the suction nozzle 44 was determined and converted to an optical density, thereby determining the concentrations of glucose and total bilirubin in the test sample.

When the images picked up by the CCD camera were processed by LUZEX-SE, with respect to the center portions of the images of GLU-P and TBIL-P, the detected light amount in the range of 1.4 mm in the longitudinal direction X 1.4 mm in the lateral direction was calculated by the image processing. At this time, a magnification of 0.33 times of the optical system was used, and thus the measurement was carried out by 42 pixels in the longitudinal direction X 42 pixels in the lateral direction, that is, by pixels whose pixel number was equal to 1764. In order to confirm whether the measurement result based on the CCD camera was right or not, the concentrations of glucose and total bilirubin in the test sample were determined by using an automatic clinical examination device 7170 made by Hitachi, Ltd. Table 4 shows the above result. At this time, the measurement wavelength was different between GLU-P and TBIL-P slides, and thus the measurement was carried out while the wavelength of the interference filter was successively varied every 5 seconds as shown in Table 5.

As described above, it has been found that the dry type analysis device 50 can quickly carry out the measurement by a simple operation without leakage of erythrocyte. This was the same result as achieved when the upper member 30 and the lower member 40 were joined to each other by ultrasonic fusion. Accordingly, it is clear that liquid can be filtered and analyzed by the dry type analysis device of the present invention.

Here, the dry chemistry reagent for two items was used as the dry type analysis element 54, however, the number of items may be suitably increased.

TABLE 4

Component value in whole blood quantified by CCD detection

|  | Value calculated by CCD detection [mg/dL] | Measurement value of Hitachi 7170 [mg/dL] |
|---|---|---|
| Glucose | 82 | 90 |
| Total bilirubin | 0.84 | 0.40 |

TABLE 5

Sequence of irradiating light while successively varying wavelength and light amount

| Order | Wavelength [nm] |
|---|---|
| 1 | 505 |
| 2 | 540 |

* Order successively varying like 1 → 2 → 1 → 2 → 1 → . . .

According to the present invention, by forming the plural members so that they are engageable with one another so as to be air-tight and water-tight under reduced pressure, air-tightness and water-tightness necessary for filtration can be maintained by filtration under reduced pressure without fusing and coupling the plural members by ultrasonic fusion or the like. Accordingly, a liquid filtering instrument and a dry type analysis device which are simple in construction and inexpensive can be provided, and thus it is suitable for disposable use.

The entire disclosure of each and every foreign patent application from which the benefit of foreign priority has been claimed in the present application is incorporated herein by reference, as if fully set forth.

What is claimed is:

1. A liquid filtering instrument for filtering a liquid under pressure-reduced filtration, the liquid filtering instrument comprising:
   a filter member receiving a filter for a liquid,
   a holder member that stocks a filtered liquid passing through the filter for a liquid, and
   a single seal member in a fitting portion between the filter member and the holder member wherein the seal member is a porous membrane filter;
   wherein said filter member and said holder member are separated by a partition wall that permits fluid communication there between, said partition wall having a step portion which projects into said filter member, and wherein said porous membrane filter is interposed at the fitting portion between the inner side wall of said filter member and the outer peripheral surface of said step portion so that a cross-section of said porous membrane filter is U-shaped; and
   wherein the filter member and the holder member are capable of being fitted so as to be substantially air-tight and water-tight when a pressure is reduced.

2. The liquid filtering instrument according to claim 1, wherein the filter for a liquid comprises a fiber having a diameter of 10 μm or less.

3. The liquid filtering instrument according to claim 1, wherein the filter for a liquid comprises a glass fiber.

4. The liquid filtering instrument according to claim 3, wherein a surface of the glass fiber is coated with a polymer.

5. The liquid filtering instrument according to claim 3, wherein the glass fiber is subjected to an acid treatment, and then a surface of the glass fiber is coated with a polymer.

6. The liquid filtering instrument according to claim 4, wherein the polymer is an acrylate polymer.

7. The liquid filtering instrument according to claim 4, wherein the polymer is a poly(alkoxy acrylate).

8. The liquid filtering instrument according to claim 1, wherein the liquid filtering instrument is disposable.

9. The liquid filtering instrument according to claim 1, wherein the liquid is a body fluid.

10. The liquid filtering instrument according to claim 9, wherein the body fluid is a blood.

11. The liquid filtering instrument according to claim 1, wherein the liquid is a liquid for examining an environment-related material.

12. The liquid filtering instrument according to claim 1, wherein the liquid is a liquid for examining a food product.

13. The liquid filtering instrument according to claim 1, wherein the liquid is a liquid used for research in natural science.

14. A liquid filtering instrument for filtering a liquid under pressure-reduced filtration, the liquid filtering instrument comprising:
   a filter member receiving a porous membrane seal member at a fitting portion;
   a holder member that stocks liquid filtered through the porous membrane seal member;
   a single porous membrane seal member in a fitting portion between the filter member and the holder member;
   wherein said filter member and said holder member are separated by a partition wall that permits fluid communication there between, said partition wall having a step portion which projects into said filter member, and wherein said porous membrane seal member is interposed at the fitting portion between the inner side wall of said filter member and the outer peripheral surface of said step portion so that a cross-section of said porous membrane seal member is U-shaped; and
   wherein the filter member and the holder member are capable of being fitted so as to be substantially air-tight and water-tight when a pressure is reduced.

* * * * *